(12) United States Patent
Savareigo

(10) Patent No.: US 6,656,374 B2
(45) Date of Patent: Dec. 2, 2003

(54) POST ETCH INSPECTION SYSTEM

(75) Inventor: Nissim Savareigo, Ashdod (IL)

(73) Assignee: Orbotech Ltd., Yavne (IL)

( * ) Notice: Subject to any disclaimer, the term of this patent is extended or adjusted under 35 U.S.C. 154(b) by 227 days.

(21) Appl. No.: 09/824,500

(22) Filed: Apr. 2, 2001

(65) Prior Publication Data

US 2001/0035267 A1 Nov. 1, 2001

(30) Foreign Application Priority Data

Apr. 2, 2000 (IL) .................................................. 135419

(51) Int. Cl.$^7$ ................................................. G06K 1/00
(52) U.S. Cl. ............................. 216/60; 216/85; 438/8; 438/9
(58) Field of Search .................. 216/60, 85; 438/8, 438/9

(56) References Cited

U.S. PATENT DOCUMENTS

| | | | |
|---|---|---|---|
| 4,758,888 A | 7/1988 | Lapidot ....................... 358/101 |
| 5,008,743 A | 4/1991 | Katzir et al. ................ 358/101 |
| 5,058,982 A | 10/1991 | Katzir .......................... 385/33 |
| 5,153,668 A | 10/1992 | Katzir et al. ................ 356/237 |
| 5,216,479 A | 6/1993 | Dotan et al. .................. 356/73 |
| 5,369,431 A | 11/1994 | Levy et al. ................. 348/126 |
| 5,495,535 A | 2/1996 | Smilansky et al. ......... 382/145 |
| 5,619,588 A | 4/1997 | Yolles et al. ................ 382/149 |
| 5,699,447 A | 12/1997 | Alumot et al. .............. 382/145 |
| 5,705,435 A * | 1/1998 | Chen ............................. 438/8 |
| 5,774,572 A | 6/1998 | Caspi .......................... 382/141 |
| 5,774,573 A | 6/1998 | Caspi et al. ................. 382/141 |
| 6,268,226 B1 * | 7/2001 | Angell et al. ................. 438/16 |
| 6,350,361 B1 * | 2/2002 | Sexton et al. ................ 205/82 |
| 6,352,867 B1 * | 3/2002 | Couteau et al. ............... 438/8 |
| 6,409,879 B1 * | 6/2002 | Toprac et al. .......... 156/345.24 |
| 2003/0000922 A1 * | 1/2003 | Subramanian et al. ........ 216/60 |

OTHER PUBLICATIONS

Orbotech Ltd., "Vision–300AP™ AOI Series", http://www.orbotech.com/products/pcb/vision–300ap2a.html, pp. 1–2, 2001.
AEI, "AIM 2000 Plus Family of Products", pp. 1–3, Jun. 1999.
AEI, "Here's What's Happening at AEI", pp. 1–3, Jun. 1999.
Orbotech, PCB Solutions, "Vision–300AP™ Series Upgrade", pp. 1–4, 2000.

* cited by examiner

Primary Examiner—Anita Alanko
(74) Attorney, Agent, or Firm—Ladas & Parry

(57) ABSTRACT

Apparatus and method for post etching inspection of electrical circuits including an optical inspection assembly viewing an electrical circuit at various regions thereon and providing output indications of etching characteristics of the electrical circuit at the various regions and output circuitry receiving the output indications of etching characteristics of the electrical circuit at the various regions and providing an output indication of variations in the etching characteristics between at least some of the various regions.

19 Claims, 3 Drawing Sheets

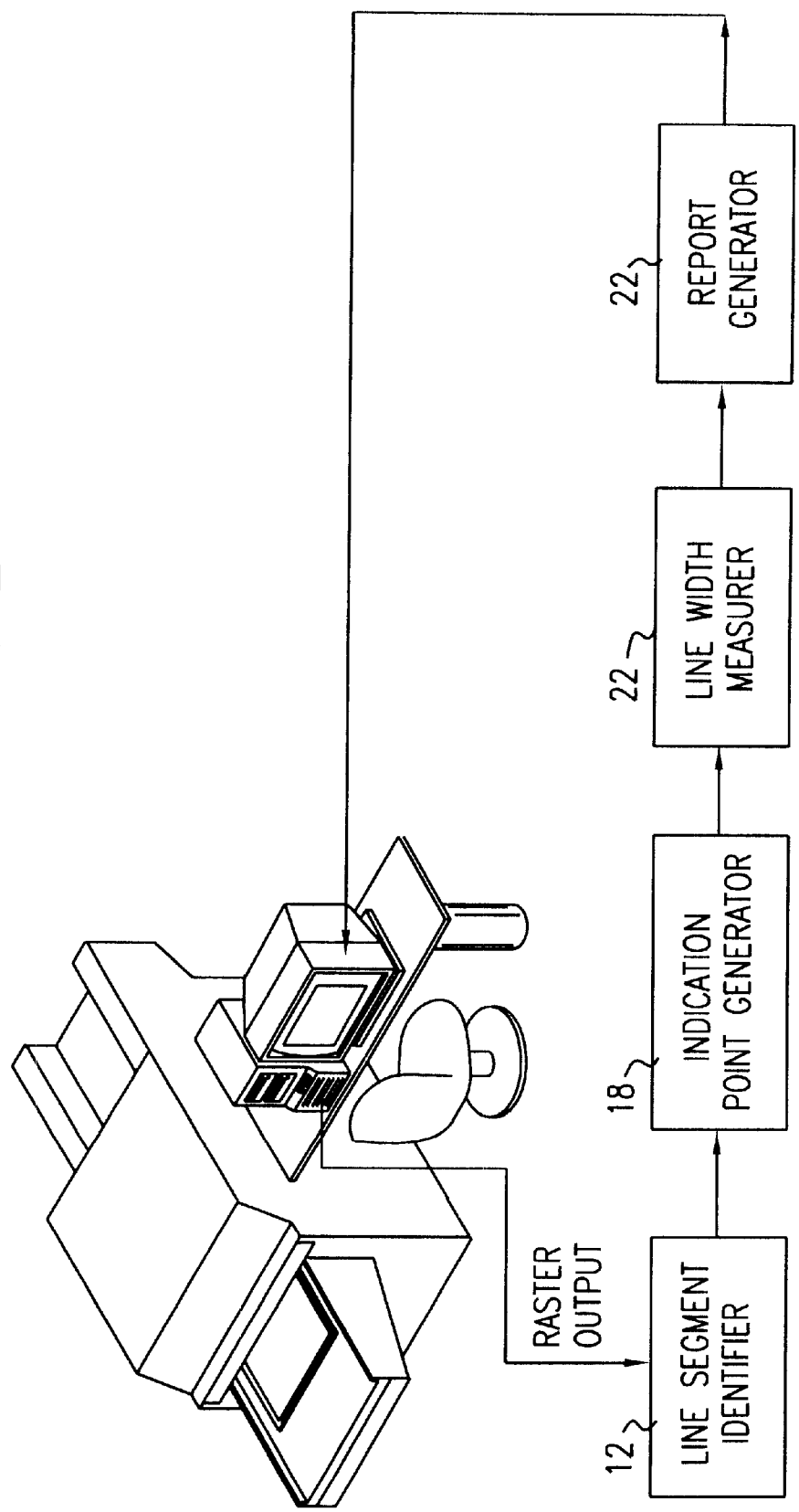

POST ETCH INSPECTION SYSTEM

FIELD OF THE INVENTION

The present invention relates to electrical circuit inspection and more particularly to automatic optical electrical circuit inspection apparatus and methods.

BACKGROUND OF THE INVENTION

There exist in the art a variety of automatic optical electric circuit inspection systems, including inter alia, systems described in whole or in part by U.S. Pat. Nos. 5,774,573; 5,774,572; 5,699,447; 5,619,588; 5,495,535; 5,369,431; 5,216,479; 5,153,668; 5,058,982; 5,008,743 & 4,758,888 of the present assignee.

There is also known a family of inspection devices, known collectively as the AIM 2000 family of Products, which are commercially available from AEI of San Diego, Calif. 92121.

SUMMARY OF THE INVENTION

The present invention seeks to provide an improved inspection system.

There is thus provided in accordance with a preferred embodiment of the present invention apparatus for post etching inspection of electrical circuits including:

an optical inspection assembly viewing an electrical circuit at various regions thereon and providing output indications of etching characteristics of the electrical circuit at the various regions; and output circuitry receiving the output indications of etching characteristics of the electrical circuit at the various regions and providing an output indication of variations in the etching characteristics between at least some of the various regions.

Preferably, the output circuitry includes at least one and most preferably all of the following elements:

a line segment identifier receiving an output from the inspection assembly and identifying conductor portions having a uniform width over at least a minimum length;

an indication point generator, which defines at least one point location which represents at least one of the location and length of a line segment having a uniform width over at least a selected minimum length;

a line width measurer, which measures the line width of each line segment having a uniform width over at least a selected minimum length;

a report generator which indicates the line width of each line segment having a uniform width over at least a selected minimum length in a graphical manner; and a report generator which indicates a statistical distribution of the line widths of line segments each having a uniform width over at least a selected minimum length in a graphical manner.

There is also provided in accordance with a preferred embodiment of the present invention a method for post etching inspection of electrical circuits including the steps of:

viewing an electrical circuit at various regions thereon and providing output indications of etching characteristics of the electrical circuit at the various regions; and receiving the output indications of etching characteristics of the electrical circuit at the various regions and providing an output indication of variations in the etching characteristics between at least some of the various regions.

Preferably, the step of providing an output indication includes at least one and most preferably all of the following elements:

line segment identification including receiving an output from the inspection assembly and identifying conductor portions having a uniform width over at least a minimum length;

indication point generation, which defines at least one point location which represents at least one of the location and length of a line segment having a uniform width over at least a selected minimum length;

line width measurement, which measures the line width of each line segment having a uniform width over at least a selected minimum length;

report generation which indicates the line width of each line segment having a uniform width over at least a selected minimum length in a graphical manner; and report generation which indicates a statistical distribution of the line widths of line segments each having a uniform width over at least a selected minimum length in a graphical manner.

Preferably the statistical distribution has sub-pixel accuracy.

BRIEF DESCRIPTION OF THE DRAWINGS

The present invention will be understood and appreciated more fully from the following detailed description, taken in conjunction with the drawings in which:

FIG. 2 is a simplified functional block diagram of the apparatus of FIG. 1; and

LIST OF APPENDICES

Appendix A is a software listing of software which, when installed in the V-300 line of automatic optical inspection devices commercially available from Orbotech Ltd. carries out the present invention in accordance with the best mode currently available to applicants.

DETAILED DESCRIPTION OF A PREFERRED EMBODIMENT

Figure 1:
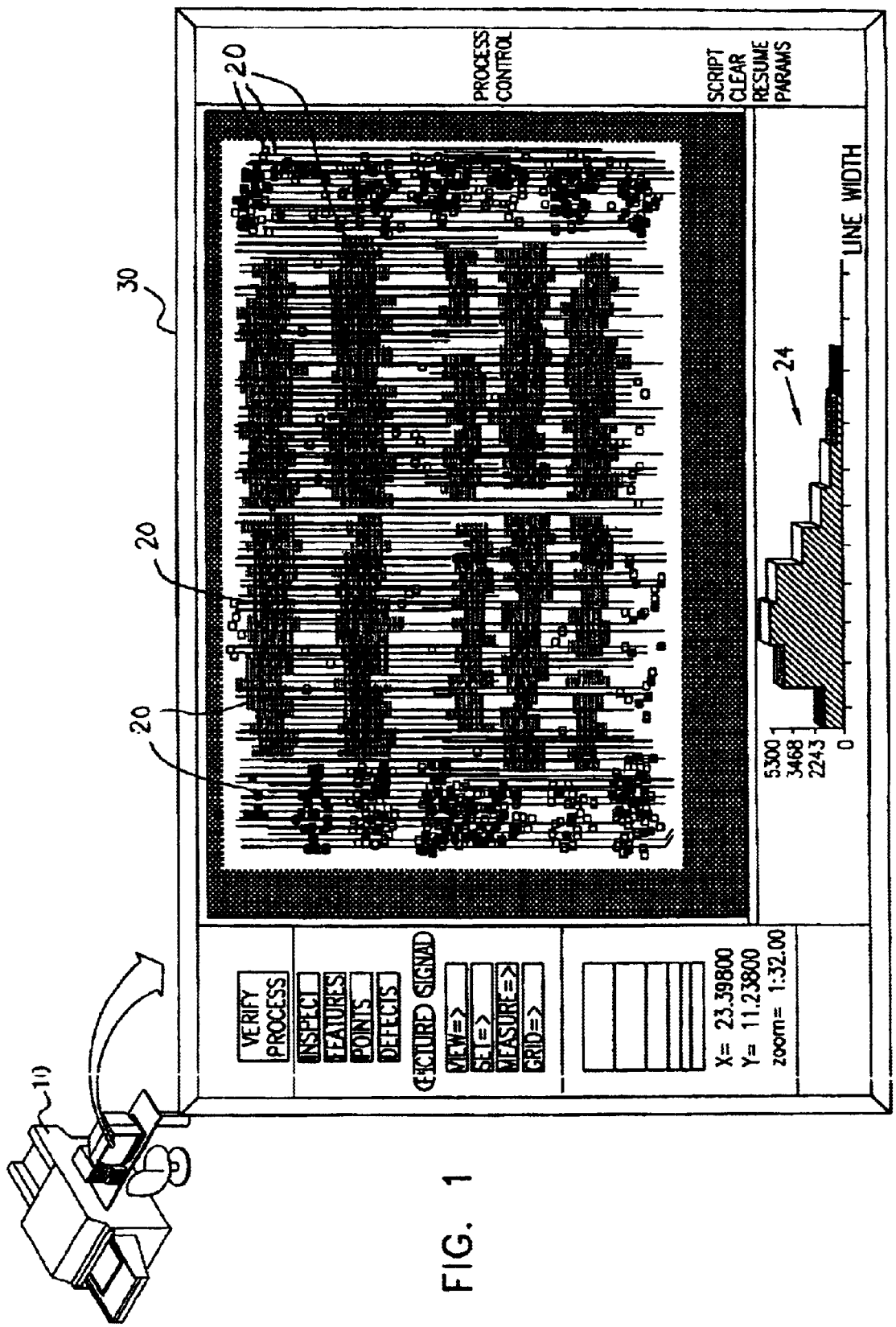
FIG. 1 is a simplified pictorial illustration of apparatus for post-etching inspection of electrical circuits constructed and operative in accordance with a preferred embodiment of the present invention.

Reference is now made to FIG. 1, which is a simplified pictorial illustration of apparatus for post-etching inspection of electrical circuits constructed and operative in accordance with a preferred embodiment of the present invention. The apparatus of FIG. 1 is preferably based on existing automated optical inspection apparatus 10 commonly used for inspecting electrical circuits, such as printed circuit boards. A preferred embodiment of such inspection apparatus is the Orbotech V-300 line of automatic optical inspection apparatus, commercially available from Orbotech Ltd. of Yavne, Israel.

The present invention provides apparatus for post etching inspection of electrical circuits comprising an optical inspection assembly viewing an electrical circuit at various regions thereon and providing output indications of etching characteristics of said electrical circuit at said various regions and output circuitry receiving said output indications of etching characteristics of said electrical circuit at said various regions and providing an output indication of variations in said etching characteristics between at least some of said various regions. For the purpose of the present invention, etching characteristics include but are not necessarily limited to line width of a conductor.

The present invention will be described hereinbelow with reference to the Orbotech V-300 line of automatic optical inspection apparatus, commercially available from Orbotech Ltd. of Yavne, Israel, it being understood that the invention is also applicable to any other suitable such apparatus, such as for example the Inspire system of Orbotech Ltd.

As seen in FIG. 1, the inspection apparatus 10, when enabled and loaded with software in accordance with a preferred embodiment of the present invention preferably provides a user sensible output 30 which indicates line width of substantially all conductors on a circuit being inspected to a selected resolution. In the illustrated embodiment, the line width is expressed in a grey scale and is superimposed over an electrical circuit pattern, seen as lines. Thus, locations corresponding to an indication point 20 are characterized by a first generally uniform line width and are indicated by a square having a first shading (for example black). Locations corresponding to an indication point 20 are characterized by a second generally uniform line width and are indicated by a square having a second shading (for example white space). Locations corresponding to an indication point 20 are characterized by a third generally uniform line width and are indicated by a square or other region having a third shading (for example a gray shading). Alternatively line width may be expressed in a color output or as height in a simulated three dimensional output or in any other suitable manner. For the purposes of clarity and simplicity, not all line widths may be represented.

Reference is now made to FIG. 2, which is a simplified functional block diagram of the apparatus of FIG. 1 and to FIGS. 3A–3E, which are diagrams useful in understanding the operation of apparatus described in FIG. 2.

As seen in FIG. 2, a raster output from inspection apparatus 10 is supplied to a line segment identifier 12, which is operative to identify all conductor portions having a uniform width over at least a minimum length. Uniformity is defined for this purpose preferably as meaning a uniform number of pixels. A typical minimum length is 8 pixels. Normally, the resolution of the apparatus 10 is selectable between 1000 to 4000 pixels per inch. In an embodiment of the invention employing, for example, the V-300 line of automated optical inspection apparatus, available from Orbotech Ltd. of Yavne, Israel, the pixels employed to calculate line widths are computational pixels which in fact are smaller than acquired pixels as acquired by optical inspection apparatus 10. As a result, the width of a line, and the minimum length of uniformity, general may be computed to sub-pixel accuracy vis-vis an acquired pixel size.

Figure 3A:
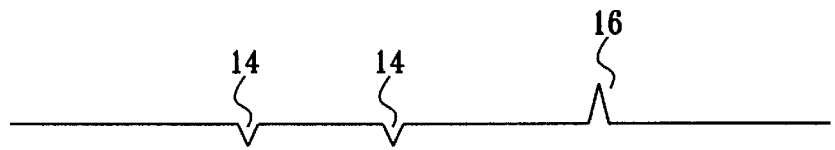
FIGS. 3A–3C are diagrams useful in understanding the operation of apparatus described in FIG. 2.
Figure 3B:
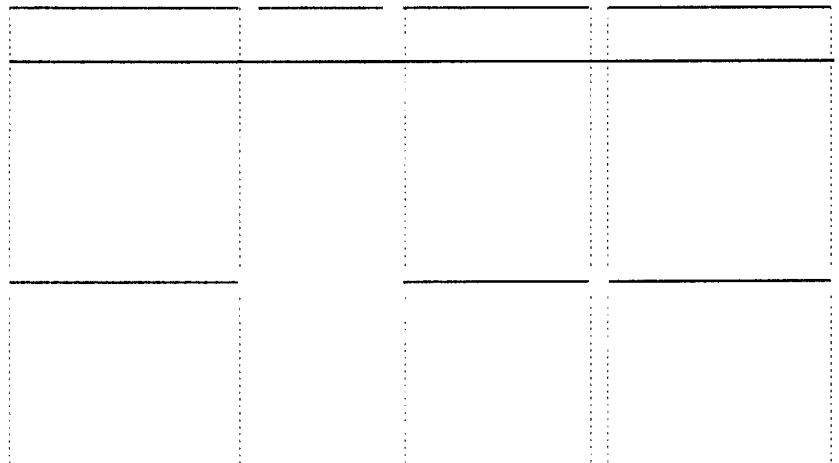

The conductors represented by the raster output may be visualized as shown in FIG. 3A, wherein local non-uniformities of width are indicated by nicks 14 and protrusions 16. Typical representations of resulting line segments having a uniform width over at least a selected minimum length are shown in FIG. 3B.

Figure 3C:
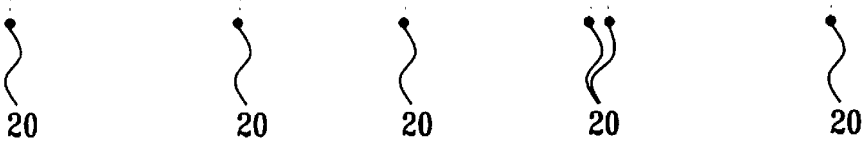

The output of line segment identifier 12 is supplied to an indication point generator 18, which typically defines one or more point locations which represent the location and length of a line segment having a uniform width over at least a selected minimum length. As seen in FIG. 3C, the indication points may be points 20 located at the beginning and end of each such line segment. Alternatively, an indication point may be at the center of each line segment. As a further alternative, indication points may be uniformly spaced along the length of each segment.

The output of indication point generator 18 is supplied to a line width measurer 22, which measures the line width of each segment. The measured width of each line segment is associated with each indication point 20 and supplied to a report generator 22, which in turn provides a display output to a display of apparatus 10.

Returning to FIG. 1, it is seen that the line width for each indication point 20, is indicated in a grey scale. Preferably a histogram indication 24 is provided of the statistical distribution of line widths so as to enable statistical evaluation and control of process parameters, possibly in an automatic manner. This statistical distribution may be employed to provide highly accurate indications of systematic variations of line widths which are spatial and or time functions. Sub-pixel accuracy regarding variations in line widths may be attained using such statistical information.

The best mode of the invention presently known to applicants may be carried out by loading the software of Appendix A onto the V-300 apparatus equipped with a suitable color output interface, in accordance with the following instructions:

1. Add new configuration called MLWHIST to /ve/init/ config file
2. Add new configuration called MLWHIST to /ve/init/ insp_mode_fields file
3. Add new inspection mode called MLW HISTOGRAM to insp_modes file
4. Add two new algorithm files MLW_ALL.ALD and MLW_AL2.ALD under /ve/init directory.

The present invention may be used for various purposes in the manufacture and testing of electrical circuits. Among these purposes are the following:

Automatic determination of line width during system set up of automated optical inspection and defect detection systems.

Highly accurate and even sub-pixel line width analysis of conductors in electrical circuits employing a large statistical sampling base. Such analysis may be carried out over the entire circuit or in specific user-defined regions.

Over-etch and under-etch detection and monitoring.

Automated manufacturing process monitoring and control.

Identification of regions in printed circuit which display systematic variations or unacceptable etch parameters.

It will be appreciated by persons skilled in the art that the present invention is not limited by what has been particularly shown and described hereinabove. Rather the scope of the present invention includes both combinations and sub-combinations of the various features described hereinabove as well as variations and modifications which would occur to persons skilled in the art upon reading the specification and which are not in the prior art.

APPENDIX A
ALGORITHM MLW_AL1
:----------------------------------------------------------------------
:     01 27-apr-93    Dave H. wrote algorithm to give a histogram of
:                     line widths
:     02 09-may-93    Dave H. copied edge smoothing sub-algorithms
:                     from MLW3
:----------------------------------------------------------------------
:     A few notes on how the algorithm works:
:          In the first half, conductors are skeletonized with
:          connectivity. Every two stages, the skeleton is written
:          to the shadow, and erased from the data. This gives many
:          stretches of skeleton in the shadow. The short ones are
:          filtered. The ends of the remaining skeletons are marked
:          in the shadow. This provides enable regions for the next half.
:          In the second half, the original picture is once again
:          skeletonized, but this time without preserving connectivity.
:          This gives better accuracy. Every time a skeleton appears,
:          and it is enabled via the shadow, the width of the skeleton
:          is reported.
:          This algorithm reports odd width conductors. MLW_AL2 reports
:          even width conductors. AL = auto learn.
:----------------------------------------------------------------------
LOCAL     min_width
LOCAL     max_width
LOCAL     width
LOCAL     first_width
LOCAL     tot_alloc
LOCAL     first
LOCAL     smoothness
:     min_width    - minimum width to report
:     max_width    - maximum width to report
:     width        - amount removed from conductors
:     first_width  - amount of first isotropic series
:     tot_alloc    - number of standard cells (sc's) allocated
:     first        - a kludge for letting $bias=min_width just once
:     smoothness   - 0 => minimum smoothing of edge
:                  - 3 => maximum smoothing of edge
:------------- parameter initialization-----------------------------
LET min_width=4
LET       max_width=60
LET       first_width=2        : report at odd intervals (width=3,5,7, ...)
LET       first=1
LET       smoothness=3
ALGORITHM MLW_AL2
:01 27-apr-93 Dave H. wrote algorithm to give a histogram of line widths
:02 09-may-93 Dave H. copied edge smoothing sub-algorithms from MLW3
LOCAL     min_width
LOCAL     max_width
LOCAL     width
LOCAL     first_width
LOCAL     tot_alloc
LOCAL     first
LOCAL     smoothness
:     min_width    - minimum width to report
:     max_width    - maximum width to report
:     width        - amount removed from conductors
:     first_width  - amount of first isotropic series
:     tot_alloc    - number of standard cells (sc's) allocated
:     first        - a kludge for letting $bias=min_width just once
:     smoothness   - 0 => minimum smoothing of edge
:                  - 3 => maximum smoothing of edge
:------------- parameter initialization-----------------------------
LET min_width=4
LET       max_width=60
LET       first_width=3        : report at odd intervals (width=4,6,8,...)
LET       first=1
LET       smoothness=3
:------------- main -----------------------------------------------
          IF L1
                    LET       $pack=1
                    LET       tot_alloc=128
          PICK      edge_[smoothness]
          PICK      start
          WCLR
                    LET       width=first_width
                    WHILE     width<max_width
                              WADD      width\O\E
                              PICK      skel_with_connectivity -continued

```
                              IF (width>=(min_width-1))&(width<(max_width-2))
                                    PICK mark_skel_and_delete_skel
------------------------------ main ------------------------------
     IF L1
                    LET      $pack=1
                    LET      tot_alloc=128
          PICK      edge_[smoothness]
          PICK      start
          WCLR
                    LET      width=first_width
                    WHILE    width<max_width
                             WADD     width\O\E
                             PICK     skel_with_connectivity
                             IF (width>=(min_width-1))&(width<(max_width-2))
                                    PICK mark_skel_and_delete_skel
          ENDIF
                    LET      width=width+2
                    ENDWHILE
                    PICK     mark_skel_and_delete_all
                    PICK     filter_skel_and_mark_open
          WCLR
          LET width=first_width
                    LET      $step=2
                    WHILE    width<max_width
                             WADD width\O\E
                             PICK     skel_no_connectivity
                             IF       width>=(min_width-1)
                                      IF     first=1
                                                  LET first=0
                                                  LET $bias=(width-1)
                                      ENDIF
                                      PICK         report_skel
                                      LET          $bias=0
                             ENDIF
                             LET      width=width+2
                    ENDWHILE
          PICK      null
          ELSE
                    LET tot_alloc=8
                    PICK null
          ENDIF
ENDALGORITHM
SUBALG   skel_with_connectivity
G        hg#
L
E
SUBALG   skel_no_connectivity
G        hg#nc
L
E
SUBALG   start
P
hgd2s
hgns
E
SUBALG   edge_0
P
hgcr_nl
E
SUBALG   edge_1
P
hgiht_nl
hgicr
E
SUBALG   edge_2
P
hgibp_nl
hgicr
E
SUBALG   edge_3
P
hgibp_nl
hgbp
hgicr
E
SUBALG   mark_skel_and_delete_skel
P
hgmkskel
E
```

-continued

```
SUBALG   mark_skel_and_delete_all
P
hgmkskde
E
SUBALG   report_skel
: report skeleton on F, clear shadow on skeleton
P
hgskelfc
E
SUBALG   filter_skel_and_mark_open
P
hgswap
hgmkskl
hghatxcs          10
hgnds
hgOrp             2
hgndcls
hgmkopnf
hgnd
E
SUBALG   null
P
TRANSPAR
$check_sc         tot_alloc-1
E
ENDIF
                    LET      width=width+2
                  ENDWHILE
                  PICK       mark_skel_and_delete_all
                  PICK       filter_skel_and_mark_open
         WCLR
         LET width=first_width
                  LET        $step=2
                  WHILE      width<max_width
                    WADD width\O{E
                    PICK     skel_no_connectivity
                    IF       width>=(min_width-1)
                             IF     first=1
                                    LET first=0
                                    LET $bias=(width-1)
                             ENDIF
                             PICK   report_skel
                             LET    $bias=0
                    ENDIF
                    LET      width=width+2
                  ENDWHILE
         PICK     null
         ELSE
                  LET tot_alloc=8
                  PICK null
         ENDIF
ENDALGORITHM
SUBALG   skel_with_connectivity
G        hg#
L
E
SUBALG   skel_no_connectivity
G        hg#nc
L
E
SUBALG   start
P
hgd2s
hgns
E
SUBALG   edge_0
P
hgcr_nl
E
SUBALG   edge_1
P
hgiht_nl
hgicr
E
SUBALG   edge_2
P
hgibp_nl
hgicr
E
```

```
                       -continued

SUBALG   edge_3
P
hgibp_nl
hgbp
hgicr
E
SUBALG   mark_skel_and_delete_skel
P
hgmkskel
E
SUBALG   mark_skel_and_delete_all
P
hgmkskde
E
SUBALG   report_skel
: report skeleton on F, clear shadow on skeleton
P
hgskelfc
E
SUBALG   filter_skel_and_mark_open
P
hgswap
hgmkskl
hghatxcs           10
hgnds
hgOrp              2
hgndcls
hgmkopnf
hgnd
E
SUBALG   null
P
TRANSPAR
$check_sc          tot_alloc-1
E
```

What is claimed:

1. A method for post etching inspection of electrical circuits, comprising:

viewing an electrical circuit at various locations thereon and providing output indications of a width of a conductor line on said electrical circuit at said various locations along a length of the conductor line; and receiving said output indications of said width of a conductor line on said electrical circuit at said various locations and providing an output indication of variations in an etching characteristic between at least some of said various locations, said etching characteristic corresponding to a line width of the conductor line being generally uniform at least over a minimum length of the conductor line.

2. A method according to claim 1 and wherein said providing an output indication of a width of a conductor line comprises:

receiving an output from an inspection assembly and identifying portions of a conductor line having a uniform width over at least a minimum length.

3. A method according to claim 2 and wherein said providing an output indication of a width of a conductor line also comprises:

indication point generating, which defines at least one point location which represents at least one selected from the group consisting of: the location and length of a line segment having a uniform width over at least a selected minimum length.

4. A method according to claim 1 and wherein said providing an output indication of a width of a conductor line comprises:

indication point generating, which defines at least one point location which represents at least one selected from the group consisting of: the location and length of a line segment having a uniform width over at least a selected minimum length.

5. A method according to claim 3 and wherein said providing an output indication of a width of a conductor line also comprises:

measuring line width of each line segment having a uniform width over at least a selected minimum length.

6. A method according to claim 2 and wherein said providing an output indication of a width of a conductor line also comprises:

measuring a line width of each line segment having a uniform width over at least a selected minimum length.

7. A method according to claim 1 and wherein said providing an output indication of a width of a conductor line comprises:

measuring a line width of each line segment having a uniform width over at least a selected minimum length.

8. A method according to claim 3 and wherein said providing an output indication of variations in an etching characteristic also comprises:

generating a report which indicates a line width of each line segment having a uniform width over at least a selected minimum length in a graphical manner.

9. A method according to claim 2 and wherein said providing an output indication of variations in an etching characteristic also comprises:

generating a report which indicates a line width of each line segment having a uniform width over at least a selected minimum length in a graphical manner.

10. A method according to claim 1 and wherein said providing an output indication of variations in an etching characteristic comprises:

generating a report which indicates a line width of each line segment having a uniform width over at least a selected minimum length in a graphical manner.

11. A method according to claim 1 and wherein said providing an output indication of variations in an etching characteristic comprises:

generating a report which indicates a statistical distribution of a line width of respective line segments each having a uniform width over at least a selected minimum length in a graphical manner.

12. A method according to claim 11 and wherein said statistical distribution has sub-pixel accuracy.

13. A method according to claim 2 and wherein said providing an output indication of variations in an etching characteristic comprises:

generating a report which indicates a statistical distribution of a line width of line segments each having a uniform width over at least a selected minimum length in a graphical manner.

14. A method according to claim 13 and wherein said statistical distribution has sub-pixel accuracy.

15. A method according to claim 3 and wherein said providing an output indication of variations in an etching characteristic comprises:

generating a report which indicates a statistical distribution of a line width of respective line segments each having a uniform width over at least a selected minimum length in a graphical manner.

16. A method according to claim 15 and wherein said statistical distribution has sub-pixel accuracy.

17. A method according to claim 4 and wherein said providing an output indication of variations in an etching characteristic comprises:

generating a report which indicates a statistical distribution of the line widths of line segments each having a uniform width over at least a selected minimum length in a graphical manner.

18. A method according to claim 17 and wherein said statistical distribution has sub-pixel accuracy.

19. A method according to claim 10 and wherein said providing an output indication of variations in an etching characteristic comprises:

generating a report which indicates a statistical distribution of the a line width of line segments each having a uniform width over at least a selected minimum length in a graphical manner.

* * * * *